US008229566B2

(12) United States Patent
Li

(10) Patent No.: US 8,229,566 B2
(45) Date of Patent: Jul. 24, 2012

(54) METHOD AND APPARATUS OF BREATHING-CONTROLLED ELECTRICAL STIMULATION FOR SKELETAL MUSCLES

(76) Inventor: Sheng Li, Bronx, NY (US)

( * ) Notice: Subject to any disclaimer, the term of this patent is extended or adjusted under 35 U.S.C. 154(b) by 1064 days.

(21) Appl. No.: 12/146,176

(22) Filed: Jun. 25, 2008

(65) Prior Publication Data

US 2009/0326606 A1 Dec. 31, 2009

(51) Int. Cl.
*A61B 5/08* (2006.01)
*A61N 1/36* (2006.01)
(52) U.S. Cl. .......................... 607/48; 600/529
(58) Field of Classification Search .............. 607/48, 607/62; 600/529, 532, 538, 540
See application file for complete search history.

(56) References Cited

U.S. PATENT DOCUMENTS

| 6,360,740 | B1 * | 3/2002 | Ward et al. ............... 128/200.24 |
| 6,819,957 | B1 | 11/2004 | Le |
| 2005/0288732 | A1 * | 12/2005 | Schuler et al. ................. 607/48 |
| 2006/0206167 | A1 * | 9/2006 | Flaherty et al. ................ 607/48 |
| 2008/0058873 | A1 | 3/2008 | Lee et al. |
| 2008/0058892 | A1 | 3/2008 | Haefner et al. |
| 2009/0312826 | A1 * | 12/2009 | Penny et al. .................. 607/149 |

OTHER PUBLICATIONS

Apkarian et al., 1991, "Stretch Reflex Inhibition Using Electrical Stimulation in Normal Subjects and Subjects with Spasticity," J. Biomed. Eng., 13:67-73.
Bolton et al., 2004, "Electromyogram-Triggered Neuromuscular Stimulation and Stroke Motor Recovery of Arm/Hand Functions: A Meta-Analysis," Journal of the Neurological Sciences, 223:121-127.
Chae et al., 2000, "A Critical Review of Neuromuscular Electrical Stimulation for Treatment of Motor Dysfunction in Hemiplegia," 12 Assist. Technol., 33-49.
Chae et al. , 2003, "Intramuscular Hand Neuroprosthesis for Chronic Stroke Survivors," The American Society of Neurorehabilitation, 17:109-117.
Chae et al., 2003, "Neuromuscular Electrical Stimulation for Motor Relearning in Hemiparesis," Phys. Med. Rehabil. Clin. N. Am., 14:S93-S109.
Chae et al., 1998, "Neuromuscular Stimulation for Upper Extremity Motor and Functional Recovery in Acute Hemiplegia," Stroke, 29:975-979.
Dewald et al., 1996, "Long-Lasting Reductions of Spasticity Induced by Skin Electrical Stimulation," IEEE Trans. Rehabil. Eng., 4:231-242.
Ikeda et al., 2007, "The Valsalva Maneuver Revisited: The Influence of Voluntary Breathing on Isometric Muscle Strength," Journal of Strengthen and Conditioning Research (in press).
Kamper et al., 2001, "Impairment of Voluntary Control of Finger Motion Following Stroke: Role of Inappropriate Muscle Coactivation," Muscle & Nerve, 673-681.
Kimberley et al., 2004, "Electrical Stimulation Driving Functional Improvements and Cortical Changes in Subjects with Stroke," Exp. Brain. Res., 154:450-460.
Li et al., 2007, "Effects of Voluntary Breathing on Force Responses to Electrical Stimulation (ES) of Finger Extensors: A Pilot Study," 12th Annual Conference of the International FES Society, Philadelphia, PA.
Li et al., 2006, "Forced Ventilation Increases Variability of Isometric Finger Forces," Neuroscience Letters, 412:243-247.

(Continued)

*Primary Examiner* — Carl H Layno
*Assistant Examiner* — Yun Haeng H Lee
(74) *Attorney, Agent, or Firm* — Sutherland Asbill & Brennan LLP

(57) ABSTRACT

Methods and devices are provided such that electrical stimulation can be delivered to a patient's skeletal muscles in response to certain respiratory signals, such as when voluntary breathing is detected.

17 Claims, 6 Drawing Sheets

OTHER PUBLICATIONS

Li et al., 2006, "Influences of Ventilation on Maximal Isometric Force of the Finger Flexors," Muscle & Nerve, 34:651-655.

Sieler, et al., 2008, "Modulation of Electrical Stimulation Response of Finger Extensors by Voluntary Breathing," NWCSM Annual Meeting, Feb. 29-Mar. 2, 2008, Seattle, Washington.

Stackhouse, 2008, "Electrical Stimulation of Muscle for Control of Movement and Posture," Clinical Electrophysiology: Electrotherapy and Electrophysiologic Testing, 3rd ed., Lippincott Williams & Wilkins, Baltimore, MD, 239-274.

* cited by examiner

METHOD AND APPARATUS OF BREATHING-CONTROLLED ELECTRICAL STIMULATION FOR SKELETAL MUSCLES

GRANT SUPPORT DISCLOSURE

This invention was made, at least in part, with funding from the National Institutes of Health (1R15NS053442-01A1). Accordingly, the United States Government has certain rights in this invention.

FIELD OF THE INVENTION

The present invention relates generally to the electrical stimulation of skeletal muscles, and more particularly to a method and apparatus of breathing-controlled electrical stimulation of skeletal muscles.

BACKGROUND OF THE INVENTION

Neuromuscular electrical stimulation is well known in the art and is used for a variety of clinical applications, including as a method for strengthening skeletal muscles. Typically, a conventional protocol of preset frequency, duration and intensity of electrical stimulation is prescribed to a patient (Stackhouse 2008). Electrical stimulation, particularly electromyogram (EMG)-triggered neuromuscular stimulation, has been used for many years in clinical settings to facilitate post-stroke motor recovery of finger extension impairments (Heckmann et al. 1997; Chae et al. 1998; Francisco et al. 1998; Cauraugh et al. 2000; Crisan and Garner 2001; Cauraugh and Kim 2002; Bocker and Smolenski 2003; Chae 2003; Bolton et al. 2004; de Kroon et al. 2005).

Roughly one third of all patients who experience a stroke have some residual impairment of the upper extremity (Parker et al. 1986; Gray et al. 1990; Nakayama et al. 1994), with a major impairment being of hand function (Trombly 1989). Common post-stroke hand function impairments include a stereotypically flexed resting posture of the wrist and fingers and an inability to extend fingers voluntarily. According to the literature, the contributing factors include biomechanical alterations, such as muscle atrophy (O'Dwyer et al. 1996); contractures (Metoki et al. 2003) and increased muscle stiffness (Dietz et al. 1991; Ibrahim et al. 1993); and neurological changes, such as wrist and finger flexor hypertonia—spasticity (Powers et al. 1988; Powers et al. 1989; Thilmann et al. 1991; Kamper and Rymer 2000; Kamper and Rymer 2001; Kamper et al. 2003), excessive coactivation of flexors and extensors (Hammond et al. 1988; Dewald et al. 1995), and reduced reciprocal inhibition (Nakashima et al. 1989; Baykousheva-Mateva and Mandaliev 1994). A recent study assessed the relative contributions of these mechanisms to overall finger and hand impairment in chronic hemiparetic stroke survivors and found that weakness in grip strength and finger extension strength accounted for the greatest portion of deficits in hand motor control after stroke (Kamper et al. 2006). As such, strengthening of finger (wrist) extensors and spasticity reduction in finger flexors are extremely important for improvement of hand function in stroke patients.

The EMG-triggered electrical stimulation protocol involves initiation by the patient of a voluntary contraction for a specific movement until the muscle activity (as measured by EMG) reaches a threshold level. When the muscle activity reaches the threshold level, it triggers an electrical stimulus to the target muscles, which facilitates the patient's movements (Heckmann et al. 1997; Chae et al. 1998; Francisco et al. 1998; Cauraugh et al. 2000; Crisan and Garner 2001; Cauraugh and Kim 2002; Bocker and Smolenski 2003; Chae 2003; Bolton et al. 2004; de Kroon et al. 2005). This intervention protocol has been found superior to passive neuromuscular stimulation in motor recovery, most likely due to the active engagement of patients during electrical stimulation therapy (Chae and Yu 2000; Chae 2003; Bolton et al. 2004; Kimberley et al. 2004). Electrical stimulation has been shown to produce immediate reductions in spasticity that may last from minutes to a few hours (Dewald et al. 1996). It has been reported that long-term users (greater than 16 months) may have longer lasting reductions in spasticity (Apkarian and Naumann 1991). However, the effectiveness of current electrical stimulation techniques on spasticity reduction remains controversial (Stackhouse 2008).

Further, the use of EMG-triggered electrical stimulation is associated with a few disadvantages, including in the finger/wrist rehabilitation context. First, EMG-triggered electrical stimulation requires voluntary activation of the muscles, by finger/wrist extension, to a certain preset threshold level. This requirement limits its application, especially for patients with moderately to severely impaired finger extension. Second, it requires "clean" EMG signals from the targeted muscle(s). This may be problematic when surface EMG signals are utilized. Though improved by using intramuscular EMG signals, this technique imposes other problems, including convenience, compliance and cost. Lastly and most importantly, inappropriate coactivation of finger flexors and extensors may cause serious problems when using assisted electrical stimulation (Kamper and Rymer 2001). For example, when patients try to assist the stimulation to the finger extensors, hand opening is significantly reduced due to inappropriate coactivation (Kamper and Rymer 2001) and finger flexor hypertonia (Chae and Hart 2003). Kamper and Rymer observed that attempts of voluntary metacarpao-phalangeal (MCP) joint extension actually resulted in MCP joint flexion in some hemiparetic patients (Kamper and Rymer 2001).

The clinical applications of EMG-triggered electrical stimulation for wrist/finger motor recovery are thus limited, and similar drawbacks to those discussed above are associated with EMG-triggered electrical stimulation in the other applications for which it is available. Moreover, as noted, passive neuromuscular stimulation has been found inferior to EMG-triggered stimulation for motor recovery.

Therefore, it would be desirable to have an improved system for delivering electrical stimulation to skeletal muscles.

SUMMARY OF THE INVENTION

A breathing-controlled electrical stimulation device and methods of use are provided, such that delivery of electrical stimulation to target muscles can be synchronized with a patient's voluntary breathing to take advantage of the discovered coupling between voluntary breathing and non-respiratory skeletal muscles.

The invention provides improved methods and devices for synchronizing neuromuscular electrical stimulation with voluntary breathing. One object of the present invention is to provide methods and devices which enable the use of neuromuscular electrical stimulation for a broader range of clinical applications. Another object of the present invention is to provide methods and devices which enhance the effectiveness of electrical stimulation to skeletal muscles. Another object of the present invention is to provide methods and devices which avoid the excessive coactivation problems associated with prior art electrical stimulation systems. The invention particularly provides methods and devices which enhance the effectiveness of motor recovery for stroke patients, based on the finger flexion-expiration, finger extension-inspiration coupling (Li & Laskin 2006). These and many other advantages and features of the invention will become apparent to those skilled in the art upon reading the present specification of the preferred embodiments.

In one aspect, methods for breathing-controlled electrical stimulation are provided. The method can comprise collecting a patient's respiratory signal; interpreting the respiratory signal to detect at least one respiratory parameter capable of differentiating voluntary breathing from autonomic breathing; and delivering electrical stimulation to a patient's target muscles when voluntary breathing is detected. Alternatively, the method of breathing-controlled electrical stimulation can comprise collecting a patient's respiratory signal; interpreting the respiratory signal to detect the value of at least one respiratory parameter which is capable of differentiating voluntary breathing from autonomic breathing; comparing the detected value of the at least one respiratory parameter with a preset threshold value; and delivering electrical stimulation to a patient's muscles when the detected value meets the preset threshold value. In certain embodiments of these methods, the detected respiratory parameter is airflow rate. In other embodiments of the methods, electrical stimulation is delivered only when the detected respiratory parameter indicates forced inspiration. In further embodiments, electrical stimulation is delivered to the patient's muscles through surface electrodes. In preferred embodiments, the patient's target muscles which receive electrical stimulation are in the arms or legs. In additional preferred embodiments, the patient's target muscles are in the wrists or fingers.

The methods can be used for rehabilitation following a stroke. The methods can also be used for rehabilitation following a traumatic brain injury. In further embodiments, the methods can be used in patient populations with different neurological disorders, such as spinal cord injury, cerebral palsy, or multiple sclerosis. In addition, the methods can be used in healthy individuals for performance enhancement.

In another aspect, a device for breathing-controlled electrical stimulation is provided. The device includes a respiratory signal collector adapted to receive a respiratory signal; a respiratory signal monitor adapted to interpret the respiratory signal to detect the value of at least one respiratory parameter; a control circuit adapted to compare the detected value of the at least one respiratory parameter value to a preset threshold value, further wherein the control circuit sends a trigger command when the detected value reaches the threshold value; and an electrical stimulation delivery controller adapted generate electrical stimulation upon receipt of the trigger command from the control circuit. In one embodiment, the respiratory signal is collected by a face mask. In one embodiment, the detected respiratory parameter can differentiate voluntary breathing from autonomic breathing. In a preferred embodiment, the detected respiratory parameter is airflow rate. In a further embodiment, airflow rate is one of multiple respiratory parameters detected by the device.

The device can include surface electrodes which are adapted to deliver electrical stimulation to a patient's skeletal muscles. Alternatively, the device can include implantable electrodes which are adapted to deliver electrical stimulation to a patient's skeletal muscles. In one embodiment, a single electrical pulse is delivered to the patient's target muscles corresponding to each trigger command. In another embodiment, a series of electrical pulses is delivered to the patient's target muscles corresponding to each trigger command. In certain embodiments of the device, the patient's target muscles which receive electrical stimulation are in the arms or legs. In another preferred embodiment, the patient's target muscles are in the wrists or fingers.

BRIEF DESCRIPTION OF THE DRAWINGS

The objects and advantages of the present invention will be better understood and more readily apparent when considered in conjunction with the following detailed description and accompanying drawings which illustrate, by way of example, preferred embodiments of the breathing-controlled electrical stimulation system and in which.

DETAILED DESCRIPTION OF THE PREFERRED EMBODIMENTS

Figure 1:
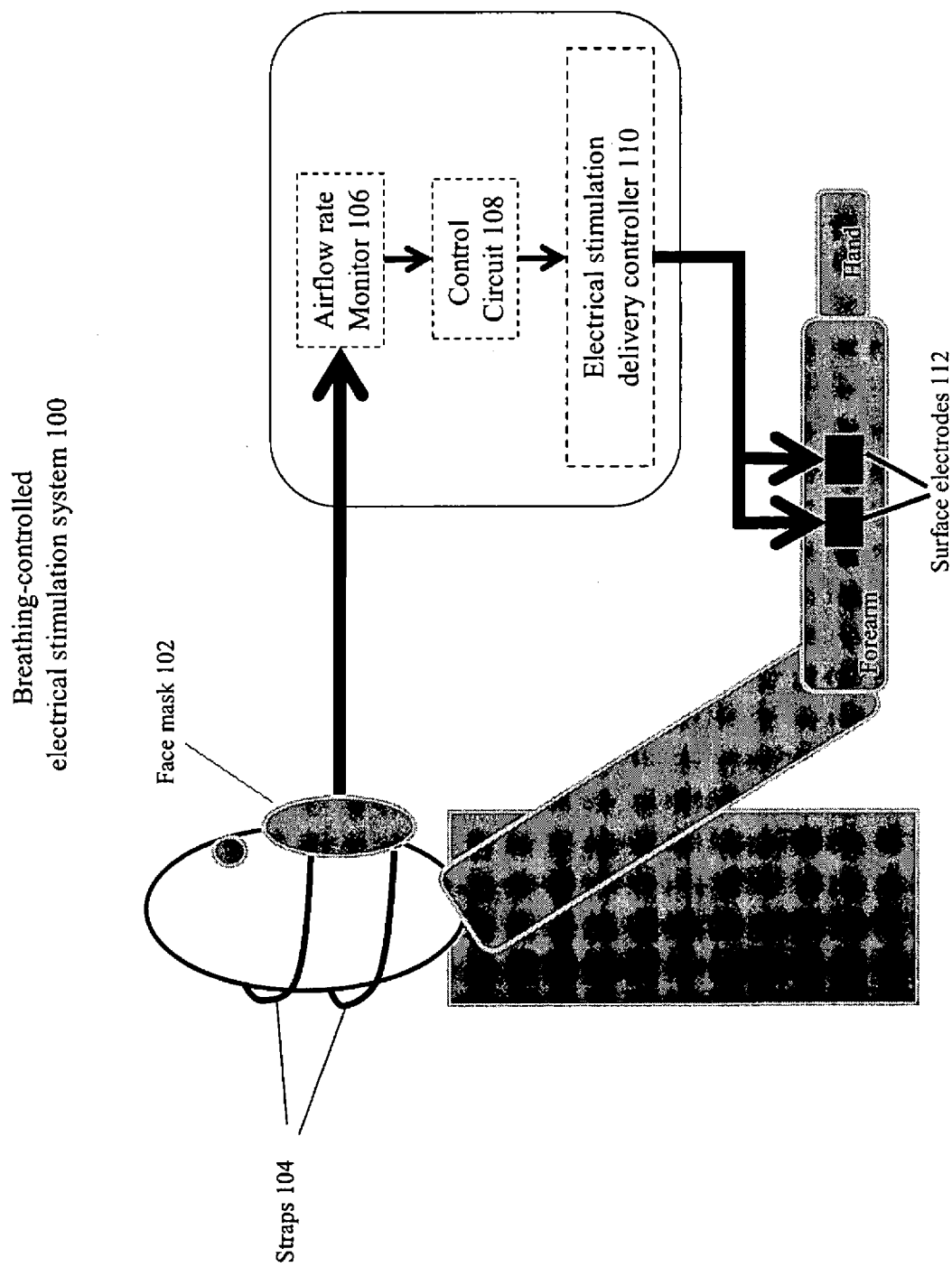
FIG. 1 is an illustration of one embodiment of the breathing-controlled electrical stimulation system.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Recent research has led to the discovery of the phenomenon of respiratory-motor coupling during voluntary breathing. Voluntary breathing, or forced inhalation and exhalation, is different from automatic breathing. Automatic control of breathing occurs at the brain stem level through activation of the cortical respiratory center. During voluntary breathing, humans voluntarily suppress this automatic control of breathing. Voluntary breathing is associated with cortical activation within the primary motor cortex. The use of non-respiratory skeletal muscles, for example finger flexors/extensors and arm and leg muscles, is also associated with cortical activation, in the motor cortical areas in particular. The two types of cortical activation are distinctly different, indicating that non-respiratory muscles are not related to respiratory activities. As such, the breathing-associated cortical activation in the primary motor cortex could act in concert directly or indirectly with the descending motor drive from the primary motor cortex to the non-respiratory skeletal muscles.

Respiratory-motor coupling has been observed in both large and small muscle groups (Li and Laskin 2006; Li and Yasuda 2007; Ikeda et al. in press). In particular, it has been reported that there is a coupling between finger flexion and expiration, and between finger extension and inspiration (Li and Laskin 2006; Li et al. 2007; Li and Yasuda 2007). According to this finger flexion-expiration, finger extension-inspiration coupling, forceful inspiration facilitates finger extension and forceful expiration facilitates finger flexion during voluntary breathing. Studies using transcranial magnetic stimulation (TMS) (Hartley et al. 2008) and electrical stimulation (Li et al. 2007; Sieler et al. 2008) have provided evidence that the coupling is largely mediated by intrinsic neurophysiological mechanisms. Taken together, the performance and function of non-respiratory skeletal muscles is influenced during voluntary breathing, largely via activation of the cortical respiratory center. The same coupling effect may be achieved by activation of the cortical respiratory center by means other than voluntary breathing, such as transcranial magnetic stimulation (TMS) or transcranial electrical stimulation (TES).

Improved methods and devices are provided for controlling neuromuscular electrical stimulation by voluntary breathing. The new methods and devices of breathing-controlled electrical stimulation are based on the intrinsic physiological coupling between the respiratory and motor systems. The new methods and devices broaden clinical applications of electrical stimulation and enhance the effectiveness of electrical stimulation to skeletal muscles. In one example embodiment, the methods and devices are used for hand rehabilitation in stroke patients based on the finger flexion-expiration, finger extension-inspiration coupling. In another embodiment, the methods and devices are applied to post-stroke rehabilitation of other skeletal muscles, such as those in the arms and legs. In further embodiments, the methods and devices can be used in patient populations with different neurological disorders, for example patients with traumatized brain injury, spinal cord injury, cerebral palsy, or multiple sclerosis, or in healthy patients for performance enhancement.

The breathing-controlled electrical stimulation system can be further understood with reference to the exemplary, non-limiting embodiments illustrated in FIGS. 1-6.

Figure 2:
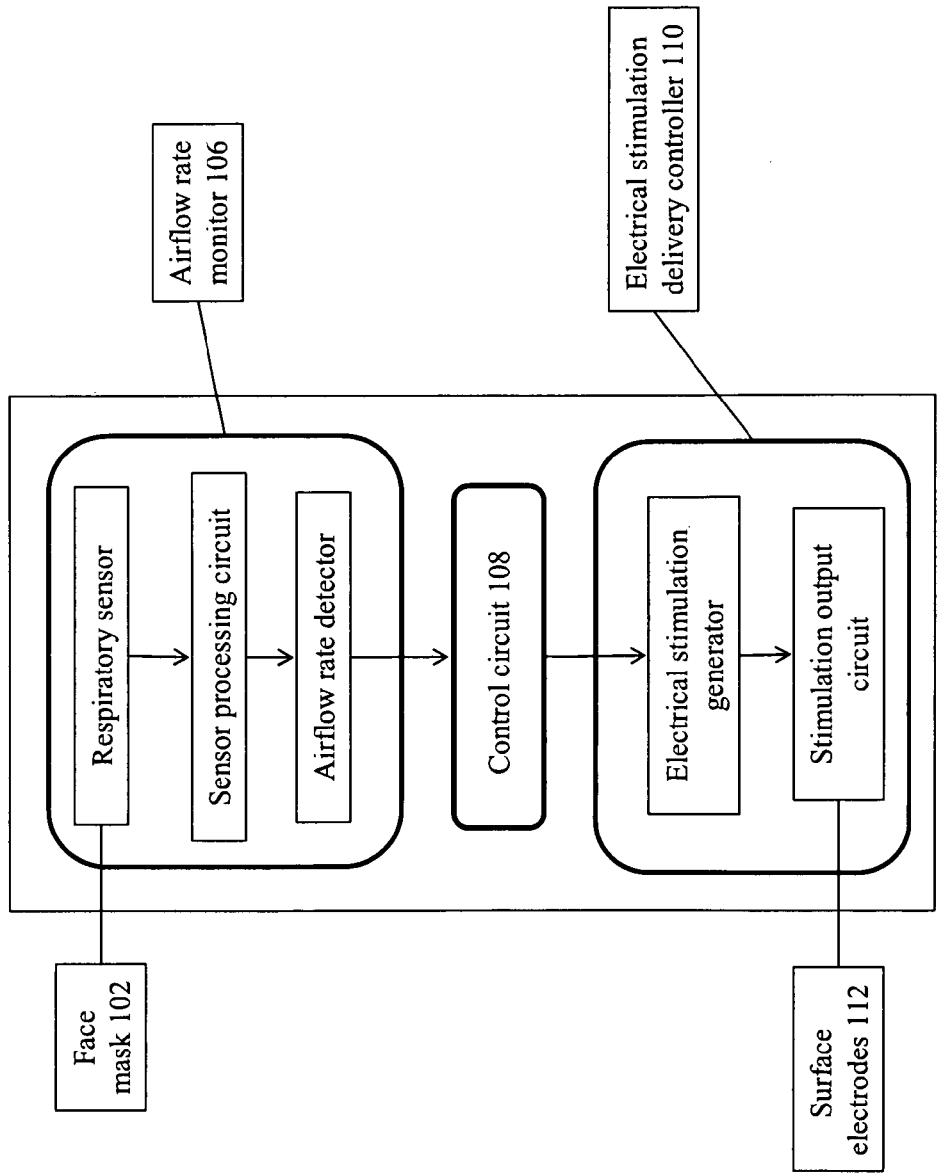
FIG. 2 is a block diagram showing functional components of one embodiment of the breathing-controlled electrical stimulation system.

One embodiment of the breathing-controlled electrical stimulation system is shown in FIG. 1. The breathing-controlled electrical stimulation system 100 triggers the delivery of neuromuscular electrical stimulation based on the airflow rate during voluntary breathing. The system receives a respiratory signal, processes the signal, and based on the signal triggers the delivery of electrical pulses to target skeletal muscles. The breathing-controlled electrical stimulation system 100 comprises a face mask 102 with attached securing straps 104, an airflow rate monitor 106, a control circuit 108, an electrical stimulation delivery controller 110, and a plurality of electrodes 112. The system has three major operational components: the airflow rate monitor 106, the control circuit 108, and the electrical stimulation delivery controller 110. FIG. 2 is a block diagram which provides additional details regarding an example embodiment of each operational component.

The face mask 102 collects the respiratory signal from the patient's breathing. The respiratory signal is a physiological signal that is indicative of respiratory activities. The respiratory signal can encompass several respiratory parameters, including respiratory cycle length, inspiration period, expiration period, non-breathing interval, tidal volume, breathing rate, and airflow rate. The use of a face mask 102 to collect a patient's respiratory signal is well known in the art, and the face mask 102 could have a variety of designs so long as it works to achieve this purpose. Example embodiments of the face mask 102 may include pressure transducers, temperature sensors, humidity sensors, gas sensors, such as oxygen or carbon dioxide, or any sensor combination thereof. The aforementioned sensors may be implemented by many known sensor devices, such as mechanical, strain gauge, piezoelectric, microelectromechanical, pyroelectric, photoelectric, vibrating, capacitance, or optical based sensors, or any combination thereof.

In the embodiment of FIG. 1, the face mask 102 is secured to the patient's face by securing straps 104. The face mask 102 preferably has a tight fit against the patient's face. The patient may be allowed to breathe using both the mouth and nose. Alternatively, depending on the design of face mask 102 or other respiratory signal collector, the patient may be directed to breathe through the mouth or nose exclusively. In other embodiments, the respiratory signal could be collected by a variety of known mechanisms other than a face mask. In one embodiment, for example, the patient breathes directly from his or her mouth into a tube. Another embodiment includes a nasal tube or cannula, which is inserted into or placed around the patient's nasal passages and may be clipped to the patient's nose to secure it in place.

In the embodiment of FIG. 1, the face mask 102 is coupled to an airflow rate monitor. The respiratory signal collected by the face mask 102 is continuously fed to the airflow rate monitor 106. The airflow rate monitor 106 processes the respiratory signal to determine the airflow rate of the patient's breathing.

The airflow rate is the main parameter used to differentiate automatic breathing from voluntary breathing and is used as the triggering-signaling parameter in the current embodiment. However, other respiratory parameters, such as the tidal volume and the respiratory cycle length, also may be used to differentiate automatic breathing from voluntary breathing. In certain embodiments, other such parameters may be substituted as the triggering-signaling parameter, and the operational components of the system are adjusted accordingly to measure and respond to the other parameter in place of airflow rate. For example, in one embodiment the system has a tidal volume monitor instead of an airflow rate monitor, and the control circuit is designed to process and respond to a tidal volume signal threshold. In further embodiments, instead of a single trigger-signaling parameter, a combination of respiratory parameters may be used, and again, the operational components are adjusted accordingly.

FIG. 2 provides an overview of functional details of one example embodiment of the airflow monitor 106. The airflow monitor 106 shown comprises a respiratory sensor, a sensor processing circuit, and an airflow rate detector. The respiratory signal passes directly from the face mask 102 to the respiratory sensor. The respiratory sensor receives the respiratory signal, including all of the respiratory parameters mentioned above. The respiratory sensor does not process the respiratory signal, but passes it to the sensor processing circuit. The processing circuit separates the signal into the various respiratory parameters and interprets at least one parameter, in this embodiment airflow rate, into a format readable by the airflow rate detector. Even in an embodiment in which the airflow rate is the only trigger-signaling parameter, the sensor processing circuit may interpret other respiratory parameters, although these parameters do not affect the system's functioning. Upon receipt of the signal input from the processing circuit, the airflow rate detector determines the airflow rate of the patient's breathing. These functions occur quickly and continuously as the patient breathes.

The configuration shown in FIG. 2 is optional; the airflow rate monitor 106 can have a variety of configurations known in the art to perform the function of receiving a respiratory signal and detecting the airflow rate. The airflow rate monitor 106 may be a combination of hardware and software-based components, which may be implemented, for example, by a microprocessor, an integrated circuit, a field programmable gate array ("FPGA"), electronic circuitry, or any combination thereof. The airflow rate monitor 106 may further include software-based logic for performing signal processing on the received respiratory signal, such as performing transforms, filtering, unit conversion, and the like. In other embodiments, some or all of the processing functions described as being performed may be performed at least partially by the control circuit described below. Further, there is no separation required between the shown functional components of the face mask 102 or other respiratory signal collector and the airflow rate monitor 106. For example, the respiratory sensor may be a part of the face mask 102 itself, as opposed to the airflow rate monitor 106. The same options apply if the monitor is designed for another respiratory parameter, such as tidal flow volume, or a combination of respiratory parameters, as discussed above.

The control circuit 108 functions as the central controller of the system. Upon processing the respiratory signal to determine the airflow rate, the airflow rate monitor 106 sends a signal identifying the airflow rate to the control circuit 108. Through a control algorithm, the control circuit 108 determines when electrical stimulation occurs. The control algorithm is preferably software-implemented. The control algorithm may be implemented by a microprocessor, an integrated circuit, a field programmable gate array ("FPGA"), electronic circuitry, or any combination thereof, or through other hardware and/or software-based devices known to one of skill in the art. A software-implemented microprocessor-based control circuit may include a memory that stores programmed logic (for example, software). The memory may also include data utilized in the operation of operating system in some embodiments. For example, a processor may utilize the operating system to execute the programmed logic, and in doing so, may also utilize the data, which may either be stored data or data obtained through measurements or external inputs. A data bus may provide communication between the memory and the processor. Users may interface with the control circuit 108 via one or more user interface device(s), such as a keyboard, mouse, control panel, or any other devices suitable for communicating digital data to the control circuit 108. The user interface device(s) may communicate through wired communication, which may be removably coupled to the pulse generator during implantation or during servicing, or may communicate wirelessly, such as through radio frequency, magnetic, or acoustic telemetry, for example. The control circuit 108 and the programmed logic implemented thereby may comprise software, hardware, firmware, or any combination thereof. Although the control circuit 108 is described as being implemented by a single controller, multiple control circuits 108 may be employed, with each performing individual functions and/or each performing redundant functions of the other. Some of the components described may exist external to the device(s) which house the airflow rate monitor and/or the electrical stimulation delivery controller, for example, within a separate processing unit, such as a personal computer or the like, that is in communication with such device(s).

As shown, in this embodiment the control circuit 108 receives real-time information about the airflow rate, which it continuously compares with an adjustable pre-determined airflow rate threshold. When the airflow rate reaches or exceeds the pre-determined threshold, the control circuit 108 sends a trigger signal to the electrical stimulation delivery controller 110, which in turn generates an adjustable degree of electrical stimulation and delivers it through the electrodes 112. The control circuit 108 receives continuous input from the airflow rate monitor 106 and performs the algorithm continuously, such that a trigger command is sent by the control circuit 108 every time the preset threshold is reached. When the detected airflow rate is below the threshold, no trigger signal is sent by the control circuit 108. Thus, until the airflow rate threshold is reached, or between breaths which meet the threshold, breathing continues without the patient receiving neuromuscular electrical stimulation.

The threshold used by the control circuit's algorithm can be determined in various ways. According to one method, the patient's maximal inspiration airflow rate during voluntary breathing is measured prior to the procedure and used to set the threshold. The threshold can be chosen as any percentage of the maximum inhaling airflow rate during voluntary breathing. The desired percentage may vary according to the clinical application. In certain embodiments, the threshold varies from 20 percent to 60 percent of the patient's maximum inhaling airflow rate during voluntary breathing. In a preferred embodiment, the threshold is 40 percent of the patient's maximum inhaling airflow rate during voluntary breathing. If a respiratory parameter other than airflow rate is used as the trigger signal, then the threshold can be chosen as a percentage of the maximum value of that parameter during voluntary breathing or otherwise, as appropriate. Although preset, the threshold can be adjusted during treatment, as desired.

According to another method, the threshold is arbitrarily set to a value without testing before the procedure. The value can then be manually adjusted to deliver electrical stimulation at appropriate points based on the airflow rate or other parameter of the patient's voluntary breathing during treatment. The threshold can be further adjusted if the relevant parameter(s) of the patient's breathing changes during treatment (for example, as a result of breathing faster, deeper, or slower).

Figure 3:
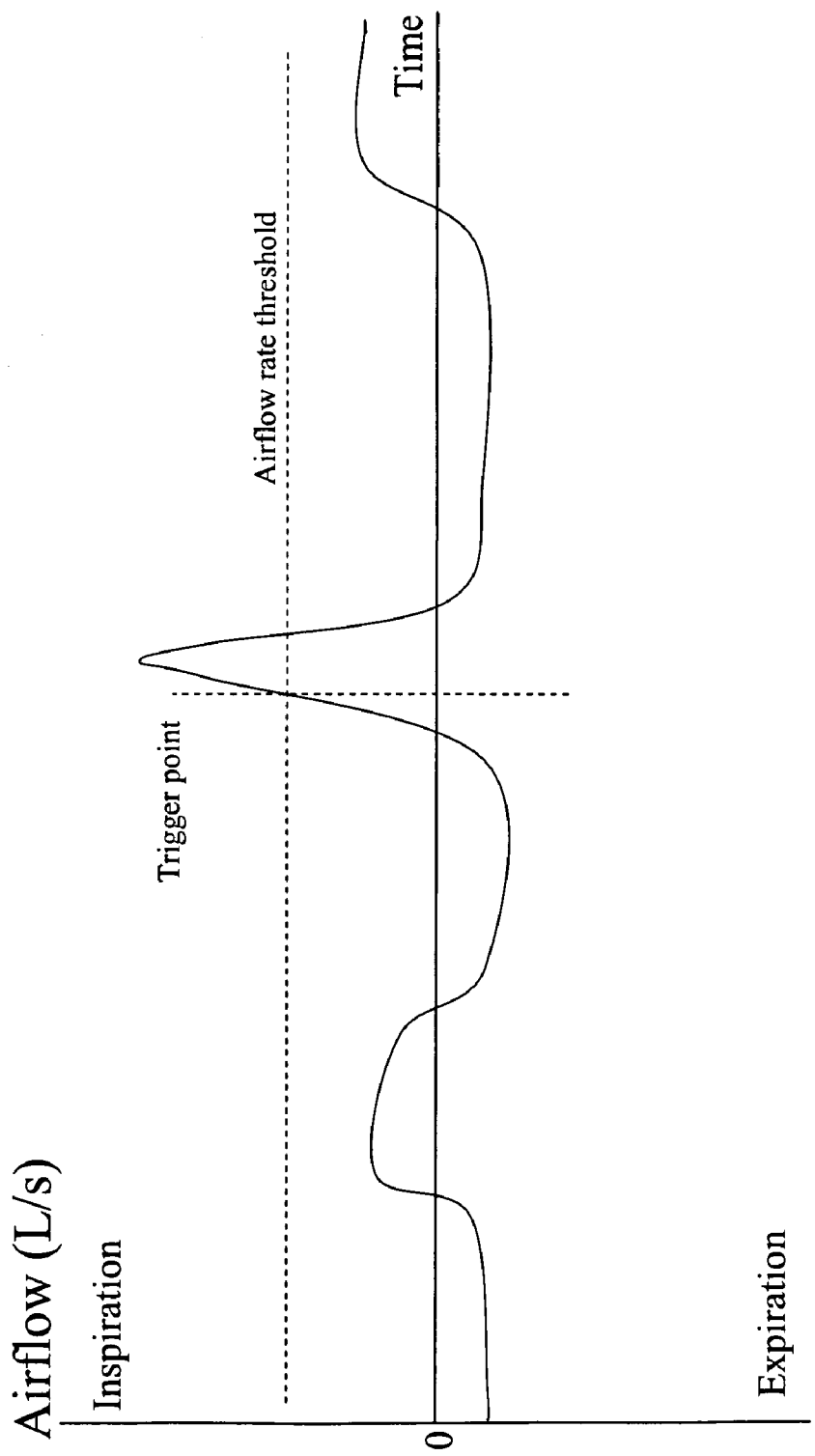
FIG. 3 is a graph showing example respiratory cycles.
Figure 4:
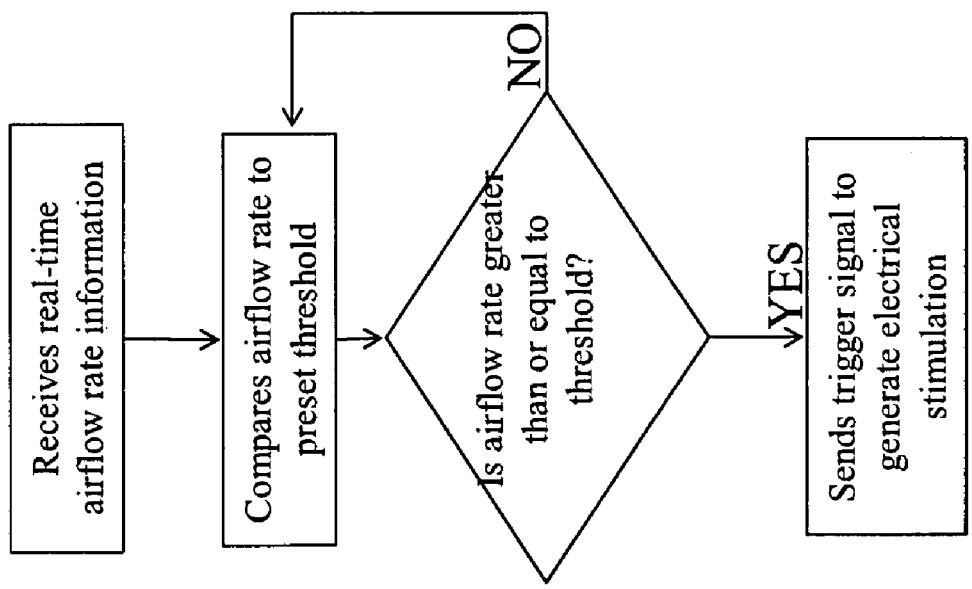
FIG. 4 is a flowchart showing one embodiment of an algorithm employed by the control circuit component of the breathing-controlled electrical stimulation system.

FIG. 3 is an illustration of example respiratory cycles. As shown, the airflow rate of the patient's breathing is measured in liters per second (L/s). Positive values indicate the inspiration phase, while negative values indicate the expiration phase. The airflow rate crossing zero indicates the transition between respiratory phases, from inspiration to expiration or vice versa. The graph shows three inspirations, represented by positive values on the graph. The second inspiration, the middle peak, represents voluntary breathing, in particular forced inspiration. The positive values to the left and right of the middle peak represent inspirations during automatic breathing. As shown, the airflow rate is significantly larger during voluntary breathing than during automatic breathing. The dashed horizontal line represents an example pre-determined airflow rate threshold which is approximately 50 percent of the patient's maximum inhaling airflow rate during voluntary breathing. The dashed vertical line represents the point in time when the real-time airflow rate reaches the threshold. At that point, as discussed, the control circuit 108 sends a trigger command to the electrical stimulation delivery controller 110 to generate an electrical pulse.

The electrical stimulation delivery controller 110 is the execution part of the system. FIG. 2 shows functional details of one embodiment of the electrical stimulation delivery controller 110. In the embodiment shown, the trigger command from the control circuit 108 is received by the electrical stimulation generator. Upon receipt of the trigger command, the electrical stimulation generator generates an electrical stimulation pulse. The pulse passes to the stimulation output circuit, which delivers the stimulation pulse to the patient's target skeletal muscle(s) via surface electrodes 112. The configuration shown in FIG. 2 is optional; the electrical stimulation delivery controller 110 can have a variety of configurations known in the art to perform the function of generating and delivering electrical stimulation upon receipt of a trigger command. An example electrical stimulation delivery controller 110 may include a power source, capacitor circuitry, which may be used to charge and discharge during defibrillation, and control logic, such as may be at least partially implemented as a hardware and/or software-based device, for example the control circuit 108 described herein, as known to one of skill in the art.

Surface electrodes 112 are connected by wires or otherwise to the electrical stimulation delivery controller 110, in particular the stimulation output circuit in this embodiment. The surface electrodes 112 are placed overlying the target muscle belly. Placement of the electrodes 112 may be adjusted to achieve on maximal isolated responses from the target muscles. The electrodes 112 are preferably adhered to the surface of the patient's skin using methods known in the art. In one embodiment, the target muscles are wrist and finger extensor muscles. In alternative embodiments, the target muscles are other skeletal muscles. In certain embodiments, the target muscles are in the patient's arms and legs. In particular, the target muscles can include the triceps, the tibialis anterior, and the peroneal muscles. Also, multiple pairs of surface electrodes 112 may be configured to deliver neuromuscular electrical stimulation to multiple target muscles at the same time. In further embodiments, instead of surface electrodes 112, the system may use implantable electrodes. The implantable electrodes 112 may be connected to the electrical stimulation delivery controller 110 via detachable wires or may have a wireless connection.

The electrical stimulation generated upon each trigger command may be a single pulse or, alternatively, a modified pattern or series of electrical stimulation pulses. The characteristics of the electrical pulse or pulses can be preset, and the desired characteristics depend on the particular clinical application. The frequency of pulses can range from approximately 2 to 100 pulses per second (pps). In a preferred embodiment, the frequency is between 20 and 50 pps. The duration of the pulses can range from approximately 20 to 600 µs. In a preferred embodiment, the duration is between 100 and 300 µs. The maximal peak amplitude of pulses, depending on whether output current or voltage is regulated, does not exceed peak values of 200 mA or 500 V, respectively. Depending on a patient's tolerance, the desired amplitude is selected during the treatment when the maximal isolated response is triggered from the target muscle(s), starting from low to high amplitudes. Although values outside of the stated ranges are contemplated by the present invention, these ranges will apply for most clinical applications.

The frequency, duration, and amplitude can be manually adjusted during the treatment, as needed. Other pulse characteristics which may be modified include the AC/DC status, the waveform, and the on/off time. If a series of pulses is generated for each trigger command, the characteristics of the pulses within the series can vary. Further, if there are multiple sets of electrodes delivering pulses to multiple muscles, different pulse characteristics may be set for each type of muscle. Typically larger skeletal muscles, such as those in the legs, can tolerate greater pulse frequency, duration, and amplitude than smaller muscles, such as those in the fingers and wrists.

One clinical application of breathing-controlled electrical stimulation is to maximize the effectiveness of neuromuscular electrical stimulation for stroke rehabilitation. As discussed herein, one example embodiment is to facilitate motor recovery of hand function in stroke patients. The feasibility and effectiveness of breathing-controlled electrical stimulation method in this example embodiment has been demonstrated in a pilot study with stroke patients.

Example 1

Figure 5:
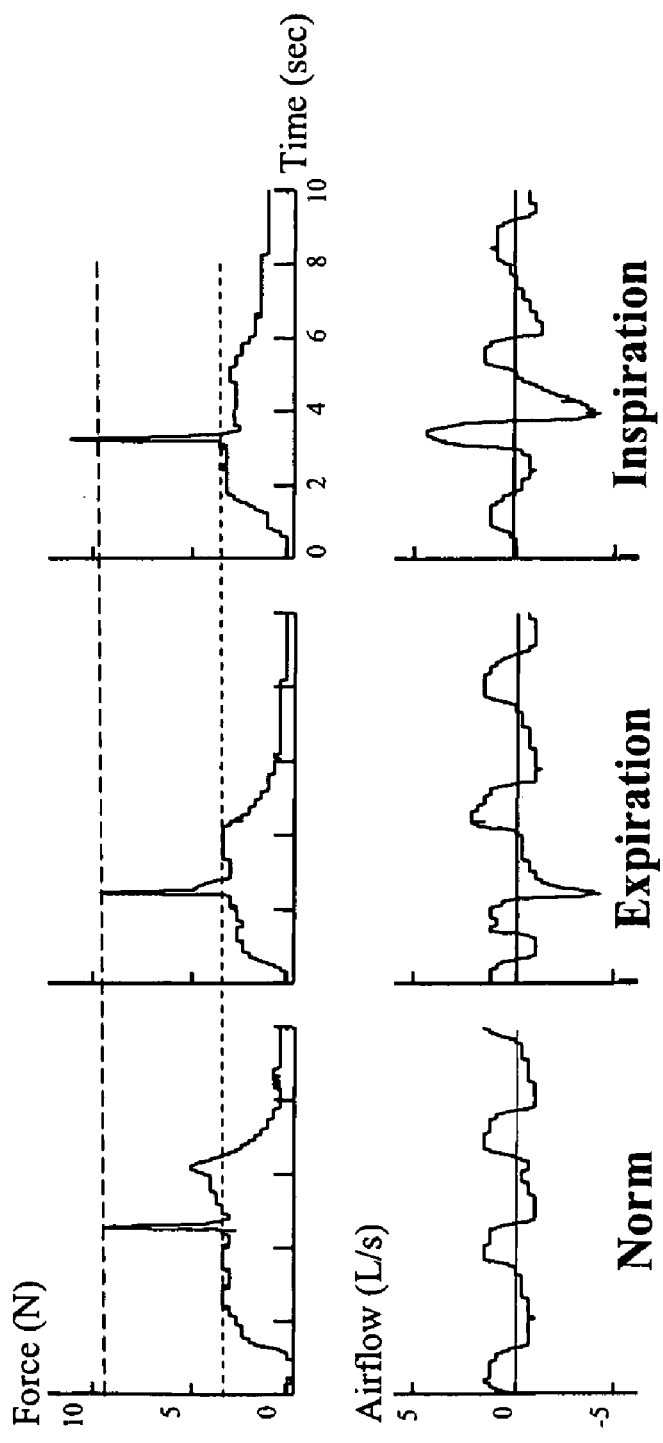
FIG. 5 is a series of graphs showing a stroke patient's responses during a study of electrical stimulation during different breathing conditions.

Data from one study is shown in FIG. 5, which supports that the most effective response to electrical stimulation can be achieved during forced inspiration. In particular, FIG. 5 shows an example response from a stroke patient when a single electrical pulse is delivered to the finger extensors during three different breathing conditions. The stroke patient (male, 75 years of age, right CVA/left hemiplegia for 22 years) had intact sensation and weak voluntary finger extension. During the electrical stimulation treatment, the patient was seated in a comfortable position in a chair with the impaired forearm stabilized in the neutral position. The patient's wrist was also stabilized in the neutral position using Velcro stripes. The mid-shafts of proximal phalanges were stabilized against four force sensors such that the metacarpophalangeal (MCP) joints were in approximately 30 degrees of flexion. The maximal finger extension force measured at MCP joints was 11.1 Newtons. The patient was instructed to maintain a 30% maximal force (represented by the lower dashed line across the force graphs) of his left finger extensors by following a visual target on the computer screen. A face mask was used to collect the patient's respiratory signal. The maximal airflow rate was measured when the patient was instructed to inhale as fast and as hard as possible (forceful inspiration) and to exhale as fast and as hard as possible (forceful expiration). The measured maximal airflow rate was 5.6 L/s for forceful inspiration and −5.9 L/s for forceful expiration. The airflow rate threshold was preset as 40% of each measured maximal airflow rate. For this patient, the threshold was 2.2 L/s for forceful inspiration and −2.4 L/s for forceful expiration. After maintaining the finger extension force following the visual target, the patient was instructed to initiate one forceful expiration (Expiration) at his convenience during a 10 second trial, and otherwise to breathe normally. This process was repeated with the patient being instructed to initiate one forceful inspiration (Inspiration) in a second trial. During a third trial, the patient was instructed to breathe only normally (Norm). The airflow rate during each of these trials is shown in L/s on the airflow graphs in FIG. 5.

The patient's real-time airflow rate, as shown on the graphs, was continuously compared with the preset threshold. A single pulse electrical stimulation was delivered to the finger extensors when the preset airflow rate threshold was reached under each of the Expiration and Inspiration conditions. A single pulse electrical stimulation was randomly triggered and delivered to the finger extensors under the Norm condition. Each pulse was a square wave with a duration of 0.1 ms and an intensity of 120 Volts. As shown on FIG. 5, a force spike occurred in response to the electrical pulse under each of the three conditions. The magnitude of force response, or force increment, was calculated as the difference between the force response peak and the mean force averaged over a 50 ms window prior to the electrical stimulation delivery. The trials had a similar baseline force, which indicates a similar background level of activation under these conditions. The force response during the Inspiration condition is visibly higher on the graphs than the force response during the Norm and Expiration conditions. The induced force increment, on average, was 5.8 Newtons, 6.2 Newtons, and 6.8 Newtons for the Normal, Expiration, and Inspiration conditions, respectively. When normalized to the force increment during normal breathing (Norm), the overall increment was 106.6% during forceful expiration and 116.6% during forceful inspiration.

Thus, the most effective response to electrical stimulation was achieved during forced inspiration.

Although enhanced responses are expected and observed when electrical stimulation is delivered to the finger extensors during forced expiration, triggering stimulation based on exhalation should be avoided in rehabilitation applications, such as motor recovery in stroke patients. Unlike forced inspiration, which facilitates primarily finger extension, forced expiration facilitates both finger flexion and finger extension. As a result, synchronizing electrical stimulation with forced expiration can lead to problematic coactivation.

Example 2

Figure 6:
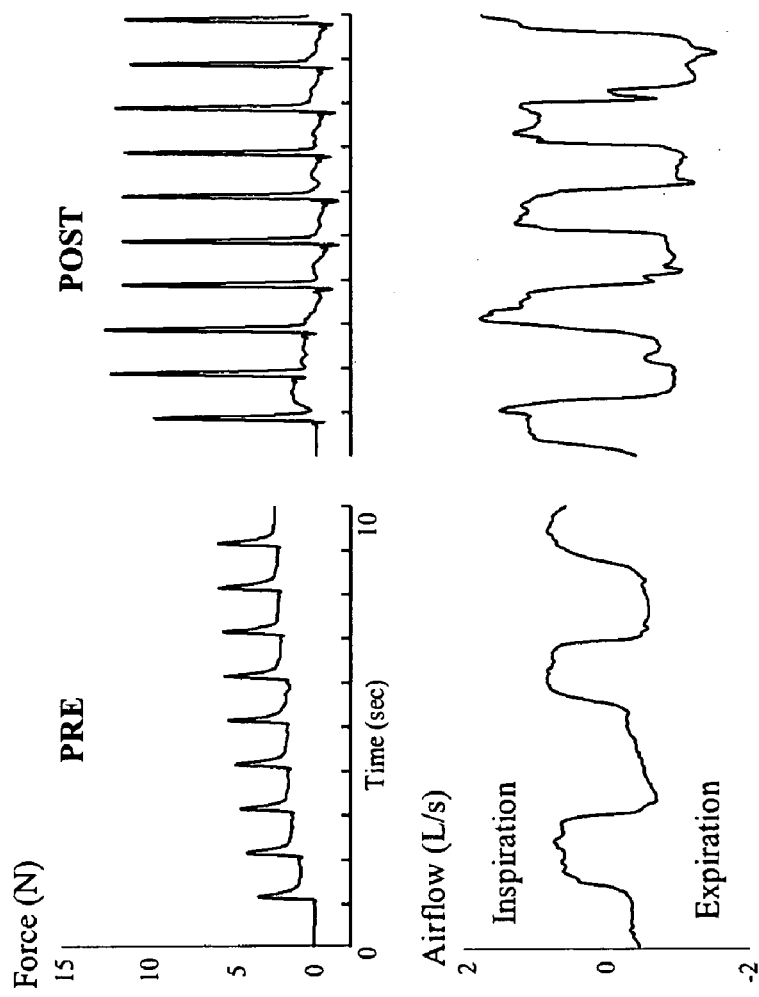
FIG. 6 is a series of graphs showing a stroke patient's responses to electrical stimulation before and after a 25 minute session using one embodiment of the breathing-controlled electrical stimulation system.

Data from another study is shown in FIG. 6, which supports the positive rehabilitation effect of breathing-controlled electrical stimulation intervention. In particular, FIG. 6 shows example responses from another stroke patient before and after a 25 minute breathing-controlled electrical stimulation intervention. The patient (male, 60 years of age, left CVA/right hemiplegia for 2 years and 2 months) had intact sensation but was without voluntary finger/wrist extension. The same experimental set-up was used for this patient as described above in the context of FIG. 5. The procedure differed from that described above. The patient was directed to initiate repeated forced inspiration, as opposed to the three breathing conditions above, and electrical stimulation was delivered only under the Inspiration condition. Single electrical pulses were triggered and delivered to his right finger extensors each time the inspiration airflow rate reached 2.0 L/s, 40% of the patient's maximal inspiration airflow rate of 5.1 L/s. Each electrical pulse was a square wave with a duration of 0.1 ms and an intensity of 160 Volts. This procedure was carried out for a total of 25 minutes, during which approximately 100 stimuli were delivered. Breaks were allowed as needed during the intervention. To test the effect of the intervention, the patient's baseline responses were measured immediately before and after the 25 minute procedure. Specifically, finger force responses were measured when the patient was at rest and when a series of electrical pulses were delivered. The duration and intensity of the electrical pulses were the same as those used during the intervention. The pre- and post-intervention responses are shown in FIG. 6. As is visible from the graphs, the stimulation-induced responses approximately doubled after the intervention. The patient also reported that his finger flexor spasticity was dramatically reduced and that the spasticity reduction lasted about three days after the intervention. This period of relief is significantly longer than the relief achieved using other methods of electrical stimulation for stroke rehabilitation.

Breathing-controlled electrical stimulation has the following advantages: 1) It encourages and requires active engagement of patients since voluntary breathing is required. Active engagement of patients is associated with better results. 2) It eliminates the problems associated with obtaining a "clean" EMG signal because no EMG signals are required. Electrical stimulation is triggered and delivered to the finger extensors when a certain breathing (inspiration) threshold, instead of EMG threshold, is reached. 3) It has broader clinical applications. Based on the intrinsic physiological coupling, breathing-controlled electrical stimulation can be applied to patients with moderate to severe impairment of finger extension, who are not candidates for EMG-triggered stimulation because they are not able to generate sufficient movement to reach the EMG muscle activity threshold. 4) It reduces the coactivation problem. The co-contraction between finger flexors and extensors and finger flexor hypertonia associated with using EMG-triggered electrical stimulation in stroke patients would occur only minimally with breathing-controlled electrical stimulation because electrical stimulation that is synchronized with forced inspiration enhances primarily activation of the finger extensors. 5) It results in long-lasting reduction of finger (wrist) flexor hypertonia. Through reciprocal inhibition mechanisms, electrical stimulation applied during the inspiration phase can inhibit activation of flexor muscles, in turn leading to reduction of flexor hypertonia in stroke patients. The advantage of using forced inspiration to trigger electrical stimulation is signified in the pilot stroke data shown in FIG. 6. Baseline responses to electrical stimulation in a patient without voluntary wrist/finger extension increased (approximately doubled) after a 25 minute intervention session. Such results have not been possible with other forms of rehabilitation. For the foregoing reasons, breathing-controlled electrical stimulation is a better choice of intervention for post-stroke motor recovery of finger extension impairments.

Breathing-controlled electrical stimulation can be used to similarly enhance the effect of neuromuscular electrical stimulation in a wide range of applications. For post-stroke patients, the device can be used to aid in the rehabilitation of any skeletal muscles other than the finger/wrist extensors. Breathing-controlled electrical stimulation can also be used in patients with different neurological disorders, including traumatic brain injury (TBI), spinal cord injury (SCI), cerebral palsy, or multiple sclerosis. The effectiveness of breathing-controlled electrical stimulation in these applications is expected, given the system's usage of respiratory-motor coupling, and such effectiveness has been supported.

Example 3

A pilot study with a chronic traumatized brain injury (TBI) patient demonstrated significant spasticity reduction. The patient (male, 27 years of age, left hemiplegia resulted from TBI for 13 years) had intact sensation of the left forearm and hand and no voluntary wrist/finger extension. The Modified Ashworth Scale of left finger flexors was 3 (0: normal, 4: fixed posture due to hypertonia). The patient received approximately 25 min of breathing-controlled electrical stimulation using the same protocol as described in Example 2. The intensity of electrical stimulation was 140 V. The duration of pulse was 0.1 ms. The preset inspiration airflow rate was 2.0 L/s, equivalent to 50% of the measured maximal inspiration airflow rate (4.0 L/s). The patient reported loosening of his left finger flexors immediately after the treatment, and the Modified Ashworth Scale was 2. This significant reduction in finger flexor hypertonia was retained until the end of 4-week follow-up from his treatment.

Breathing-controlled electrical stimulation has also been shown by two studies (Li et al. 2007, and Sieler et al. 2008) to strengthen skeletal muscles for performance enhancement for healthy individuals.

Example 4

In one pilot study (Li et al. 2007), using the experimental protocol described in Example 1, the force responses to electrical stimulation of finger extensors were measured under different breathing conditions. Three young and healthy males were instructed to produce constant isometric finger extension forces at 10%, 20%, and 30% of their maximal force, respectively. Electrical stimulation was delivered to the finger extensors during normal breathing, forced inspiration (IN) and forced expiration (OUT). The force increment, or force response to electrical stimulation, was normalized to that measured during normal breathing. The normalized increment increased considerably and consistently across all tested force levels. On average, the overall normalized increment was 153.2% during OUT and 143.2% during IN.

Example 5

In another pilot study (Sieler et al. 2008), three young and healthy females were instructed to produce constant isometric finger extension force at 10% of their maximal force or at rest. The same protocol was used as in Example 4. The normalized increment increased consistently in all three subjects both at 10% and at rest. The average normalized increased was 120.2% during OUT and 115.8% during IN.

REFERENCES

J. A. Apkarian & S. Naumann, Stretch reflex inhibition using electrical stimulation in normal subjects and subjects with spasticity, 13 J. Biomed. Eng. 67-73 (1991).
V. Baykousheva-Mateva & A. Mandaliev, Artificial feedforward as preparatory motor control in postictal hemiparesis, 34 Electromyogr. Clin. Neurophysiol. 445-448 (1994).
B. Bocker & U. C. Smolenski, Training by EMG-triggered electrical muscle stimulation in hemiparesis, 13 Motorisches lernen mittels EMG-getriggerter elektrostimulation bei hemiparese 139 (2003).
D. A. E. Bolton, J. H. Cauraugh & H. A. Hausenblas, Electromyogram-triggered neuromuscular stimulation and stroke motor recovery of arm/hand functions: A meta-analysis. 223 Journal of the Neurological Sciences 121 (2004).
J. Cauraugh, K. Light, S. Kim, M. Thigpen & A. Behrman, Chronic motor dysfunction after stroke: recovering wrist and finger extension by electromyography-triggered neuromuscular stimulation, 31 Stroke 1360-1364 (2000).
J. H. Cauraugh & S. Kim, Two Coupled Motor Recovery Protocols Are Better Than One: Electromyogram-Triggered Neuromuscular Stimulation and Bilateral Movements, 33 Stroke 1589-1594 (2002).
J. Chae, Neuromuscular electrical stimulation for motor relearning in hemiparesis, 14 Phys. Med. Rehabil. Clin. N. Am. S93-109 (2003).
J. Chae, F. Bethoux, T. Bohine, L. Dobos, T. Davis & A. Friedl, Neuromuscular stimulation for upper extremity motor and functional recovery in acute hemiplegia, 29 Stroke 975-979 (1998).
J. Chae, R. Hart, Intramuscular hand neuroprosthesis for chronic stroke survivors, 17 Neurorehabil. Neural Repair 109-117 (2003).
J. Chae & D. Yu, A critical review of neuromuscular electrical stimulation for treatment of motor dysfunction in hemiplegia, 12 Assist. Technol. 33-49 (2000).
R. Crisan & C. Garner, Effectiveness of EMG-triggered muscular stimulation in outpatients with a stroke older than one year, 7 Neurology and Rehabilitation 228 (2001).
J. R. de Kroon, M. J. Ijzerman, J. Chae, G. J. Lankhorst & G. Zilvold, Relation between stimulation characteristics and clinical outcome in studies using electrical stimulation to improve motor control of the upper extremity in stroke, 37 J. Rehabil. Med. 65-74 (2005).
J. P. Dewald, J. D. Given & W. Z. Rymer, Long-lasting reductions of spasticity induced by skin electrical stimulation, 4 IEEE Trans. Rehabil. Eng. 231-242 (1996).
J. P. Dewald, P. S. Pope, J. D. Given, T. S. Buchanan & W. Z. Rymer, Abnormal muscle coactivation patterns during isometric torque generation at the elbow and shoulder in hemiparetic subjects, 118 (Pt 2) Brain 495-510 (1995).
V. Dietz, M. Trippel & W. Berger, Reflex activity and muscle tone during elbow movements in patients with spastic paresis. 30 Ann. Neurol. 767-779 (1991).
G. Francisco, J. Chae, H. Chawla, S. Kirshblum, R. Zorowitz, G. Lewis & S. Pang, Electromyogram-triggered neuromuscular stimulation for improving the arm function of acute stroke survivors: a randomized pilot study, 79 Arch. Phys. Med. Rehabil. 570-575 (1998).
C. S. Gray, J. M. French, D. Bates, N. E. Cartlidge, O. F. James & G. Venables, Motor recovery following acute stroke, 19 Age Ageing 179-184 (1990).
M. C. Hammond, S. S. Fitts, G. H. Kraft, P. B. Nutter, M. J. Trotter & L. M. Robinson, Co-contraction in the hemiparetic forearm: quantitative EMG evaluation, 69 Arch. Phys. Med. Rehabil. 348-351 (1988).
J. Hartley, J. Smetana, M. Vannatta, J. D. Jordan & S. Li, Respiratory phase dependent changes in corticospinal excitability during voluntary breathing: a transcranial magnetic stimulation study, In: NWACSM Annual Meeting, Feb. 29-Mar. 2, 2008, Seattle, Wash. USA.
J. Heckmann, T. Mokrusch, A. Krockel, S. Warnke, T. Von Stockert, & B. Neundorfer, EMG-triggered electrical muscle stimulation in the treatment of central hemiparesis after a stroke, 7 European Journal of Physical Medicine and Rehabilitation 138 (1997).
I. K. Ibrahim, W. Berger, M. Trippel, & V. Dietz, Stretch-induced electromyographic activity and torque in spastic elbow muscles: Differential modulation of reflex activity in passive and active motor tasks, 116 Brain 971-989 (1993).
E. R. Ikeda, A. Borg, D. Brown, J. Malouf, K. M. Showers & S. Li, The Valsalva maneuver revisited: Is the Valsalva maneuver a proper breathing technique for ultimate force production?, Journal of Strengthen and Conditioning Research (In press).
D. G. Kamper, H. C. Fischer, E. G. Cruz & W. Z. Rymer, Weakness Is the Primary Contributor to Finger Impairment in Chronic Stroke, 87 Archives of Physical Medicine and Rehabilitation 1262 (2006).
D. G. Kamper, R. L. Harvey, S. Suresh & W. Z. Rymer, Relative contributions of neural mechanisms versus muscle mechanics in promoting finger extension deficits following stroke, 28 Muscle Nerve 309-318 (2003).
D. G. Kamper & W. Z. Rymer, Quantitative features of the stretch response of extrinsic finger muscles in hemiparetic stroke, 23 Muscle Nerve 954-961 (2000).
D. G. Kamper & W. Z. Rymer, Impairment of voluntary control of finger motion following stroke: role of inappropriate muscle coactivation, 24 Muscle Nerve 673-681 (2001).
T. J. Kimberley, S. M. Lewis, E. J. Auerbach, L. L. Dorsey, J. M. Lojovich, & J. R. Carey, Electrical stimulation driving functional improvements and cortical changes in subjects with stroke, 154 Exp. Brain Res. 450-460 (2004).
S. Li & J. J. Laskin, Influences of ventilation on maximal isometric force of the finger flexors, 34 Muscle Nerve 651-655 (2006).
S. Li, W. H. Park, E. R. Ikeda & C. T. Leonard, Effects of voluntary breathing on force responses to electrical stimulation (ES) of finger extensors: a pilot study, In: 12th annual conference of the International FES society, Nov. 10-14, 2007, Philadelphia, Pa. USA.
S. Li & N. Yasuda, Forced ventilation increases variability of isometric finger forces, 412 Neurosci. Lett. 243-247 (2007).

N. Metoki, Y. Sato, K. Satoh, K. Okumura & J. Iwamoto, Muscular atrophy in the hemiplegic thigh in patients after stroke, 82 Am J. Phys. Med. Rehabil. 862-865 (2003).

K. Nakashima, J. C. Rothwell, B. L. Day, P. D. Thompson, K. Shannon & C. D. Marsden, Reciprocal inhibition between forearm muscles in patients with writer's cramp and other occupational cramps, symptomatic hemidystonia and hemiparesis due to stroke, 112 Brain 681-697 (1989).

H. Nakayama, H. S. Jorgensen, H. O. Raaschou & T. S. Olsen, Recovery of upper extremity function in stroke patients: the Copenhagen Stroke Study, 75 Arch. Phys. Med. Rehabil. 94-398 (1994).

N. O'Dwyer, L. Ada & P. Neilson, Spasticity and muscle contracture following stroke, 119 Brain 1737-1749 (1996).

V. M. Parker, D. T. Wade & R. Langton Hewer, Loss of arm function after stroke: measurement, frequency, and recovery, 8 Int. Rehabil. Med. 69-73 (1986).

R. K. Powers, J. Marder-Meyer & W. Z. Rymer, Quantitative relations between hypertonia and stretch reflex threshold in spastic hemiparesis, 23 Ann. Neurol. 115-124 (1988).

R. K. Powers, S. Vanden Noven & W. Z. Rymer, Evidence of shared, direct input to motoneurons supplying synergist muscles in humans, 102 Neurosci. Lett. 76-81 (1989).

H. M. Sieler, L. S. Brandt, M. A. York & S. Li, Modulation of electrical stimulation response of finger extensors by voluntary breathing, In: NWACSM Annual Meeting, Feb. 29-Mar. 2, 2008, Seattle, Wash. USA.

S. Stackhouse, Electrical stimulation of muscle for control of movement and posture, Clinical electrophysiology:electrotherapy and electrophysiologic testing (3rd ed.), Lippincott Williams & Wilkins, Baltimore, Md., 239-274 (2008).

A. F. Thilmann, S. J. Fellows & E. Garms, The mechanism of spastic muscle hypertonus:
Variation in reflex gain over the time course of spasticity, 114 Brain 233-244 (1991).

C. A. Trombly, Occupational therapy for physical dysfunction, Williams & Wilkins, Baltimore, Md., 454-471 (1989).

What is claimed is:

1. A method of breathing-controlled electrical stimulation, comprising:
   a. collecting a patient's respiratory signal;
   b. interpreting the respiratory signal to detect at least one respiratory parameter useable for differentiating voluntary breathing from autonomic breathing; and
   c. delivering electrical stimulation to a patient's target muscles when voluntary breathing is detected, wherein said electrical stimulation is delivered only when forced inspiration is detected.

2. The method of claim 1, wherein airflow rate is the detected respiratory parameter.

3. The method of claim 1, wherein the method is used for post-stroke rehabilitation.

4. The method of claim 3, wherein the patient's target muscles are in the wrist or finger.

5. The method of claim 1, wherein the patient's target muscles are any skeletal muscles in the arm or leg.

6. The method of claim 1, wherein the application of the method is selected from the group consisting of rehabilitation following a stroke, rehabilitation following a spinal cord injury, rehabilitation following a traumatic brain injury, rehabilitation of patients with cerebral palsy, and rehabilitation of patients with multiple sclerosis.

7. The method of claim 1, wherein the method is used for performance enhancement in healthy patients.

8. The method of claim 1, wherein electrical stimulation is delivered to the patient's muscles through surface electrodes.

9. A method of breathing-controlled electrical stimulation, comprising:
   a. collecting a patient's respiratory signal;
   b. interpreting the respiratory signal to detect the value of at least one respiratory parameter which is useable for differentiating voluntary breathing from autonomic breathing;
   c. comparing the detected value of the at least one respiratory parameter with a preset threshold value; and
   d. delivering electrical stimulation to a patient's muscles when the detected value meets the preset threshold value, wherein said electrical stimulation is delivered only when forced inspiration is detected.

10. The method of claim 9, wherein airflow rate is the detected respiratory parameter.

11. The method of claim 9, wherein the preset respiratory parameter threshold is adapted to correspond to forced inspiration.

12. The method of claim 11, wherein the method is used for post-stroke rehabilitation.

13. The method of claim 12, wherein the patient's target muscles are in the wrist or finger.

14. The method of claim 9, wherein the patient's target muscles are any skeletal muscles in the arm or leg.

15. The method of claim 9, wherein the application of the method is selected from the group consisting of rehabilitation following a stroke, rehabilitation following a spinal cord injury, rehabilitation following a traumatic brain injury, rehabilitation of patients with cerebral palsy, and rehabilitation of patients with multiple sclerosis.

16. The method of claim 9, wherein the method is used for performance enhancement in healthy patients.

17. The method of claim 9, wherein electrical stimulation is delivered to the patient's muscles through surface electrodes.

* * * * *